(12) United States Patent
Kato et al.

(10) Patent No.: US 10,371,659 B2
(45) Date of Patent: Aug. 6, 2019

(54) GAS SENSOR ELEMENT

(71) Applicants: TOYOTA JIDOSHA KABUSHIKI KAISHA, Aichi (JP); DENSO CORPORATION, Aichi (JP)

(72) Inventors: Tetsuya Kato, Okazaki (JP); Satoshi Nakamura, Okazaki (JP); Hiroki Nishijima, Nisshin (JP); Makoto Ito, Kariya (JP)

(73) Assignees: TOYOTA JIDOSHA KABUSHIKI KAISHA, Toyota-shi, Aichi (JP); DENSO CORPORATION, Kariya, Aichi (JP)

(*) Notice: Subject to any disclaimer, the term of this patent is extended or adjusted under 35 U.S.C. 154(b) by 1 day.

(21) Appl. No.: 15/545,864

(22) PCT Filed: Feb. 12, 2016

(86) PCT No.: PCT/JP2016/054059
§ 371 (c)(1),
(2) Date: Jul. 24, 2017

(87) PCT Pub. No.: WO2016/147768
PCT Pub. Date: Sep. 22, 2016

(65) Prior Publication Data
US 2018/0017514 A1    Jan. 18, 2018

(30) Foreign Application Priority Data
Mar. 17, 2015    (JP) .................................. 2015-053933

(51) Int. Cl.
*G01N 27/12* (2006.01)
*G01N 27/406* (2006.01)
(Continued)

(52) U.S. Cl.
CPC ........ *G01N 27/125* (2013.01); *G01M 15/104* (2013.01); *G01N 27/4067* (2013.01);
(Continued)

(58) Field of Classification Search
CPC .. G01N 27/104; G01N 27/125; G01N 27/304; G01N 27/406; G01N 27/4067;
(Continued)

(56) References Cited

U.S. PATENT DOCUMENTS

2003/0159928 A1    8/2003   Kojima et al.
2006/0237316 A1*  10/2006   Clyde ................ G01N 27/4075
                                                                  204/424
(Continued)

FOREIGN PATENT DOCUMENTS

JP    61-241657 A    10/1986
JP    3-44659 U       4/1991
(Continued)

OTHER PUBLICATIONS

International Search Report for PCT/JP2016/054059, dated Apr. 5, 2016 (PCT/ISA/210).

*Primary Examiner* — Susan D Leong
(74) *Attorney, Agent, or Firm* — Sughrue Mion, PLLC

(57) ABSTRACT

A gas sensor element with suppressed response deterioration even when poisoned with S when fuel or exhaust gas contains ethanol and the ethanol content is high. The element includes a detection portion, which includes a solid electrolyte layer having a pair of electrodes on opposite sides thereof, a shielding layer defining a measurement target gas space with a porous diffusive resistance layer, and a reference gas space protective layer; a heat-generating portion stacked on the detection portion; and a porous protective layer surrounding the detection portion and heat-generating portion. The porous protective layer includes a
(Continued)

first porous protective layer surrounding at least the porous diffusive resistance layer, and a second porous protective layer surrounding the first porous protective layer, the detection portion and the heat-generating portion. The first porous protective layer contains none of La, Ca, or Mg, while the second porous protective layer contains at least one of them.

2 Claims, 7 Drawing Sheets

(51) Int. Cl.
*G01N 27/41* (2006.01)
*G01M 15/10* (2006.01)
*G01N 27/407* (2006.01)
*G01N 33/00* (2006.01)
*G01N 33/497* (2006.01)

(52) U.S. Cl.
CPC ..... *G01N 27/4072* (2013.01); *G01N 27/4077* (2013.01); *G01N 27/41* (2013.01); *G01N 33/0036* (2013.01); *G01N 33/0047* (2013.01); *G01N 33/497* (2013.01)

(58) Field of Classification Search
CPC ............. G01N 27/407; G01N 27/4072; G01N 27/4074; G01N 27/4075; G01N 27/4077; G01N 27/4078; G01N 27/4111; G01N 27/4114; G01N 27/4115
See application file for complete search history.

(56) References Cited

U.S. PATENT DOCUMENTS

2011/0094883 A1* 4/2011 Ito .................... G01N 27/4077
204/429
2015/0075254 A1 3/2015 Sakuma et al.

FOREIGN PATENT DOCUMENTS

| JP | 2007-121323 A | 5/2007 |
| JP | 2010-107409 A | 5/2010 |
| JP | 2014-089074 A | 5/2014 |
| JP | 2015-059758 A | 3/2015 |

* cited by examiner

GAS SENSOR ELEMENT

CROSS REFERENCE TO RELATED APPLICATIONS

This application is a National Stage of International Application No. PCT/PCT/JP2016/054059 filed Feb. 12, 2016, claiming priority based on Japanese Patent Application No. 2015-053933, filed Mar. 17, 2015, the contents of all of which are incorporated herein by reference in their entirety.

TECHNICAL FIELD

The present invention relates to a gas sensor element for detecting the concentration of a specific gas in the measurement target gas.

BACKGROUND ART

In a variety of industries, a variety of attempts has been made worldwide to reduce environmental impacts and burdens. In particular, in the automobile industry, development for promoting the spread of not only fuel-efficient gasoline engine vehicles, but also so-called eco-friendly vehicles, such as hybrid vehicles and electric vehicles, as well as for further improving the performance of such vehicles has been advanced day by day.

Measurement of the fuel consumption performance of vehicles is conducted by detecting the concentration of oxygen in the measurement target gas, such as the exhaust gas, using a gas sensor, and determining the difference between the concentration of oxygen and the concentration of oxygen in the air as a reference gas.

As a specific structure of an embodiment of a gas sensor element that constitutes such a gas sensor, an element that generally includes the following is typically known: a detection portion including a solid electrolyte layer having on the opposite sides thereof a pair of electrodes including an electrode on the measurement target gas side and an electrode on the reference gas side, a porous diffusive resistance layer (or a diffusion-controlled layer) that surrounds the electrode on the measurement target gas side with a measurement target gas space interposed therebetween, a shielding layer that defines the measurement target gas space with the porous diffusive resistance layer, and a reference gas space protective layer that surrounds the electrode on the reference gas side with a reference gas space interposed therebetween; a heat-generating portion including a heat generation source, such as a heater; and a porous protective layer (or a catalyst-carrying protective layer or a catalyst-carrying trapping layer) that surrounds the detection portion and the heat-generating portion. Output current is determined by controlled diffusion in which rich gas, such as oxygen or HC, for example, reaches the electrode on the measurement target gas side via the porous diffusive resistance layer. In the case of an A/F sensor, for example, the A/F value is detected.

The aforementioned gas sensor detects the concentration of oxygen in the exhaust gas under a high temperature atmosphere of greater than or equal to 700° C. Thus, if water droplets in the exhaust gas collide with the gas sensor element of the gas sensor, thermal shock may be generated due to partial quenching, and due to a change in the volume of the element with a change in the temperature, water-induced cracking of the element may occur, so that the sensing function may be lost, which is problematic. If a gas sensor element with the aforementioned configuration in which the detection portion and the like are surrounded by the porous protective layer is applied to address such a problem, it becomes possible to effectively suppress collision of water droplets with the detection portion and the heat-generating portion owing to the catalyst-carrying protective layer. It should be noted that Patent Literatures 1 and 2 each disclose a technology related to a gas sensor element in which the periphery of the element is surrounded by a porous protective layer made of alumina.

By the way, if inferior fuel that is distributed in some areas is used for gasoline for the aforementioned fuel-efficient gasoline engine vehicles or hybrid vehicles, it is concerned that the performance of the vehicles may degrade due to $SO_x$ poisoning (or S poisoning) that would occur with an increase in the S components in the fuel.

Thus, it is an urgent object to be achieved in the technical field to develop a gas sensor element that can, even when the gas sensor element is poisoned with S and thus may have a reduced sensor output, suppress a reduction in the sensor output due to the S poisoning.

CITATION LIST

Patent Literature

Patent Literature 1: JP 2007-121323 A
Patent Literature 2: JP 2010-107409A

SUMMARY OF INVENTION

Technical Problem

The present invention has been made in view of the foregoing problems, and it is an object of the present invention to provide a gas sensor element in which a reduction in the sensor output is suppressed even when the gas sensor element is poisoned with S as the content of S in fuel or in the exhaust gas is high.

Solution to Problem

In order to achieve the above object, a gas sensor element in accordance with the present invention includes: a detection portion including a solid electrolyte layer having a pair of electrodes on opposite sides thereof, the pair of electrodes including an electrode on a measurement target gas side and an electrode on a reference gas side, a porous diffusive resistance layer that surrounds the electrode on the measurement target gas side with a measurement target gas space interposed therebetween, a shielding layer that defines the measurement target gas space with the porous diffusive resistance layer, and a reference gas space protective layer that surrounds the electrode on the reference gas side with the reference gas space interposed therebetween; a heat-generating portion stacked on the detection portion, the heat-generating portion having a heat generation source; and a porous protective layer that surrounds the detection portion and the heat-generating portion. The porous protective layer includes a first porous protective layer and a second porous protective layer, the first porous protective layer surrounding at least the porous diffusive resistance layer, and the second porous protective layer surrounding the first porous protective layer and also surrounding the detection portion and the heat-generating portion. The first porous protective layer contains none of La, Ca, or Mg. The second porous protective layer contains at least one of La, Ca, or Mg.

In the gas sensor element of the present invention, the porous protective layer that surrounds the detection portion and the like has a two-layer stacked structure, and the first porous protective layer, which surrounds at least the porous diffusive resistance layer of the detection portion, contains none of La, Ca, or Mg, while the second porous protective layer, which surrounds the first porous protective layer, contains at least one of La, Ca, or Mg. Accordingly, it is possible to ensure the strength of the entire porous protective layer owing to the second porous protective layer that contains La and the like, while suppressing S poisoning of the porous diffusive resistance layer that is the entrance for gas having a large influence on the output change of the sensor.

Each of the first and second porous protective layers can be formed from a baked body of alumina particles and the like. The second porous protective layer contains at least one of (one of or two or more of) La, Ca, or Mg. Meanwhile, the first porous protective layer contains none of La, Ca, or Mg. It should be noted that each of the first and second porous protective layers may also be formed using ceramics other than alumina particles or an intermetallic compound.

According to the verification by the inventors, it has been known, as a result of closely examining a gas sensor that is poisoned with S, that $SO_4^{2-}$ is adsorbed strongly locally onto La in the porous protective layer, and it has been clarified that this causes an output change of the sensor in a rich condition. More specifically, HC gas being consumed for the reduction of the $SO_4^{2-}$ is the main cause for the output change, and it has been identified that the residue S in the area of the porous protective layer through which gas flows into the porous diffusive resistance layer has a particularly large influence on the output change.

Thus, by forming the first porous protective layer, which is provided in the area through which gas flows into the porous diffusive resistance layer (area that is in direct contact with the porous diffusive resistance layer), such that it does not contain La or the like, it is possible to effectively suppress the residue S in the area, and thus suppress the output change of the sensor as much as possible.

Meanwhile, although it is concerned that the first porous protective layer, which is formed of alumina, for example, may become unstable as it does not contain La or the like, and the strength of the layer may thus become low, it becomes possible to, by forming the second porous protective layer containing La and the like such that it surrounds the first porous protective layer, provide a porous protective layer without lowered strength across the entire layer.

In addition, in a preferred embodiment of the gas sensor element in accordance with the present invention, the content of the at least one of La, Ca, or Mg in the second porous protective layer is the range of greater than 0 mass % and less than or equal to 1 mass %.

The inventors have, as a result of verifying the output change of the sensor by adjusting the concentration of La in the porous protective layer in the range of greater than 0 mass % and less than or equal to 1 mass %, confirmed that, when compared with the conventional product in which the concentration of La in the porous protective layer is over 1 mass %, the output change rate of the present invention can be reduced to about ⅓ to ⅕ that of the conventional product.

In addition, in a preferred embodiment of the gas sensor element in accordance with the present invention, the first porous protective layer surrounds the porous diffusive resistance layer and the shielding layer.

The inventors have also verified that when the first porous protective layer, which does not contain La or the like, surrounds not only the porous diffusive resistance layer but also the shielding layer, that is, when the area of the detection portion that is directly surrounded by the first porous protective layer, which does not contain La or the like, is increased, it becomes possible to further increase the effect of reducing the output change.

As described above, the gas sensor element in accordance with the present invention can be applied as an air/fuel ratio sensor element (A/F sensor element) that is disposed in an exhaust system of an internal combustion engine of a vehicle and is applied to an exhaust gas feedback system, an oxygen sensor element that measures the concentration of oxygen in the exhaust gas, or a $NO_x$ sensor element that measures the concentration of air pollutants, such as $NO_x$, used for detection of deterioration of a three-way catalyst and the like.

Advantageous Effects of Invention

As can be understood from the foregoing description, according to the gas sensor element of the present invention with the configuration in which the porous protective layer, which surrounds the detection portion and the like, has a two-layer stacked structure, and the first porous protective layer, which surrounds at least the porous diffusive resistance layer of the detection portion, contains none of La, Ca, or Mg, while the second porous protective layer, which surrounds the first porous protective layer, contains at least one of La, Ca, or Mg, it is possible to ensure the strength of the entire porous protective layer owing to the second porous protective layer that contains La and the like, while suppressing S poisoning of the porous diffusive resistance layer that is the entrance for gas having a large influence on the output change of the sensor.

DESCRIPTION OF EMBODIMENTS

Hereinafter, Embodiments 1 and 2 of the gas sensor element of the present invention will be described with reference to the drawings.

Embodiments 1 and 2 of Gas Sensor Element

Figure 1:
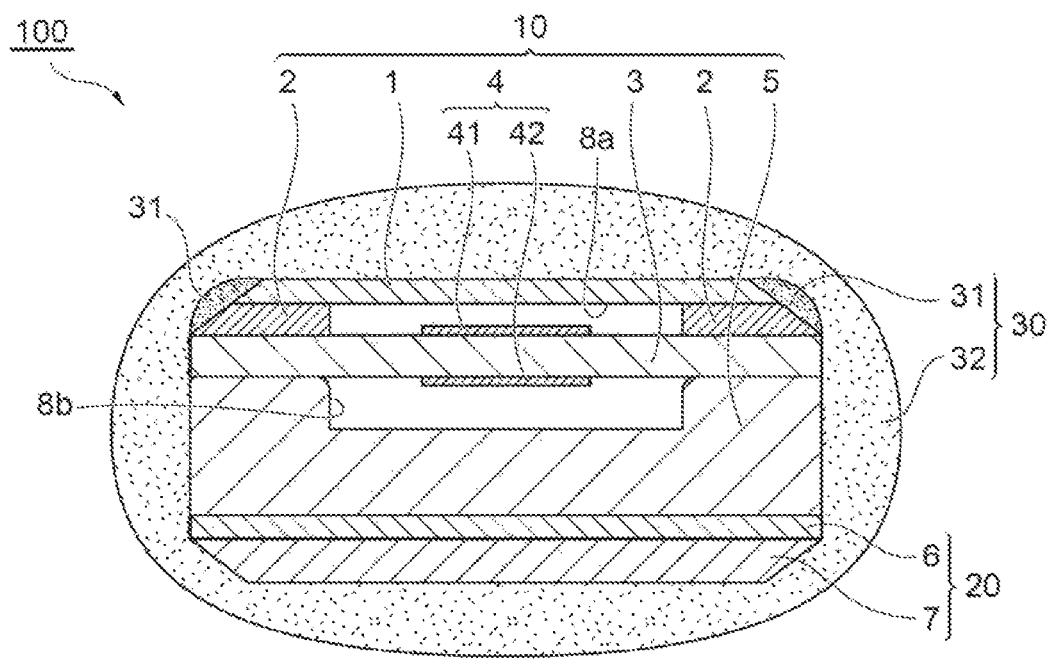
FIG. 1 is a schematic view illustrating Embodiment 1 of the gas sensor element of the present invention.
Figure 2:
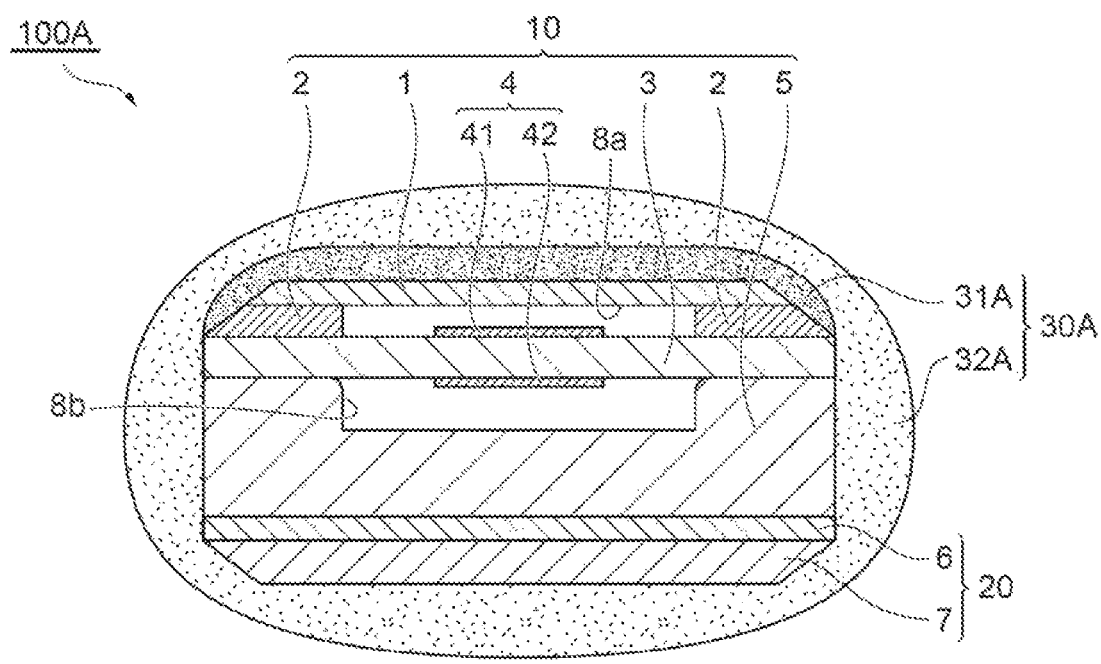
FIG. 2 is a schematic view illustrating Embodiment 2 of the gas sensor element of the present invention.

FIGS. 1 and 2 are schematic views each illustrating Embodiments 1 and 2 of the gas sensor element of the present invention.

First, a specific structure of the gas sensor element will be described with reference to FIG. 1. A gas sensor element 100 shown in FIG. 1 generally includes a detection portion 10 that detects the concentration of oxygen in the exhaust gas, a heat-generating portion 20 that is stacked on the detection portion 10, and a porous protective layer 30 that protects the periphery of the detection portion 10 and the heat-generating portion 20 against moisture in the exhaust gas and thus suppresses water-induced cracking of the detection portion 10 or the heat-generating portion 20 due to moisture that would otherwise reach the detection portion 10 or the heat-generating portion 20, and also traps lead and sulfur that are poisonous substances.

The detection portion 10 includes a solid electrolyte layer 3 having a pair of electrodes, which include an electrode 41 on the measurement target gas side and an electrode 42 on the reference gas side, on the opposite sides thereof, a porous diffusive resistance layer 2 that surrounds the electrode 41 on the measurement target gas side with a measurement target gas space 8a interposed therebetween, a shielding layer 1 that defines the measurement target gas space 8a with the porous diffusive resistance layer 2, and a reference gas space protective layer 5 that surrounds the electrode 42 on the reference gas side with a reference gas space 8b interposed therebetween.

Meanwhile, the heat-generating portion 20 includes a heat generation source 6, which includes a heater as a heating element, and a heat generation source substrate 7 that supports the heat generation source 6, and is heat-controlled so that a heated region of the gas sensor element 100 is formed and the activating temperature thereof is reached.

The corners of the detection portion 10 have cutouts that are tapered in the cross-section in FIG. 1. Such cutouts can ensure the thickness of the porous protective layer 30 at the corresponding positions of the detection portion 10, and thus can ensure the waterproof property in the region.

The solid electrolyte layer 3 is formed of zirconia, while each of the electrode 41 on the measurement target gas side and the electrode 42 on the reference gas side is formed of platinum. In addition, each of the shielding layer 1 and the reference gas space protective layer 5 has an internal structure that is impermeable to gas, and is formed of alumina.

When the gas sensor element is an air-fuel ratio sensor element, for example, it is possible to, by applying a voltage at which the oxygen concentration difference and current have a linear correlation across the pair of electrodes 4, making the measurement target gas into contact with the electrode 41 on the measurement target gas side, and making the reference gas, such as air, into contact with the electrode 42 on the reference gas side, and then measuring the value of current generated between the two electrodes in accordance with the oxygen concentration difference, identify the air-fuel ratio of the vehicle engine on the basis of the amount of the measured current.

The porous diffusive resistance layer 2 is provided at a position that defines the measurement target gas space 8a around the electrode 41 on the measurement target gas side in order to suppress the amount of the measurement target gas that is introduced to the electrode 41 on the measurement target gas side, and is configured to further introduce hydrogen gas, carbon monoxide gas, oxygen gas, and the like in the exhaust gas, which have been introduced via the porous protective layer 30 on the outer side of the porous diffusive resistance layer 2, into the measurement target gas space 8a via the porous diffusive resistance layer 2.

The porous protective layer 30 has a function of burning unburned gas, such as hydrogen gas and carbon monoxide gas, which are contained in the measurement target gas and may possibly degrade the detection accuracy of the gas sensor element 10, and also has a function of trapping poisonous substances, such as lead, silicon, and phosphorus, that may poison the electrode 41 on the measurement target gas side.

More specifically, the porous protective layer 30 includes a first porous protective layer 31 that directly surrounds the outer side of the porous diffusive resistance layer 2, and a second porous protective layer 32 that entirely surrounds the first porous protective layer 31, the detection portion 10, and the heat-generating portion 20.

Each of the first and second porous protective layers 31 and 32 is formed from a baked body of alumina particles and the like. In addition, the second porous protective layer 32 contains at least one of (one of or two or more of) La, Ca, or Mg. Meanwhile, the first porous protective layer 31 that is in direct contact with the porous diffusive resistance layer 2 contains none of La, Ca, or Mg.

As described above, by forming the first porous protective layer 31, which is provided in an area that is in direct contact with the porous diffusive resistance layer 2 and through which gas flows into the porous diffusive resistance layer 2, such that it does not contain La or the like, it is possible to effectively suppress the residue S in the area, and thus suppress the output change of the sensor as much as possible.

It has been known that $SO_4^{2-}$ is adsorbed strongly locally onto La in the porous protective layer 30, and it has been clarified that HC gas being consumed for the reduction of the $SO_4^{2-}$ is the main cause for the output change. Further, the inventors have applied a structure in which the first porous protective layer 31 does not contain La or the like based on the finding that the residue S in the area of the porous protective layer 30 through which gas directly flows into the porous diffusive resistance layer 2 has a particularly large influence on the output change.

When the first porous protective layer 31 made of an alumina material does not contain La as described above, it is concerned that the alumina forming the first porous protective layer 31 may easily become unstable, which may result in lowered strength of the first porous protective layer 31.

To address such concern, in the gas sensor element 100 shown in FIG. 1, the second porous protective layer 32, which is made of an alumina material and contains La and the like, is provided such that it surrounds the first porous protective layer 31, whereby the porous protective layer 30 for which lowering of the strength of the layer as a whole is not concerned is formed.

It should be noted that the content of at least one of La, Ca, or Mg in the second porous protective layer 32 is preferably adjusted in the range of greater than 0 mass % and less than or equal to 1 mass %.

As described below, it has been verified that when compared with the conventional product in which the concentration of La in the porous protective layer is over 1 mass %, the output change rate of the present invention can be reduced to about 1/3 to 1/5 that of the conventional product.

Hereinafter, a method for producing the gas sensor element 100 will be briefly described. After the detection portion 10 and the heat-generating portion 20 are connected together and thus are integrated, alumina slurry that does not contain La or the like is applied only to the periphery of the porous diffusive resistance layer 2, and baking is performed to form the first porous protective layer 31, so that an intermediate is produced. Such a step is repeated until the first porous protective layer 31 has a predetermined thickness.

Next, the intermediate is immersed in alumina slurry that contains La and the like, and is then pulled out of the slurry, and baking is performed. Thus, the gas sensor element 100 that is surrounded by the second porous protective layer 32 is produced. Such immersion and baking are also repeated until the second porous protective layer 32 has a predetermined thickness.

Next, Embodiment 2 of the sensor element will be described with reference to FIG. 2. A gas sensor element 100A shown in FIG. 2 has a configuration in which a first porous protective layer 31A of a porous protective layer 30A surrounds not only the porous diffusive resistance layer 2 but also the shielding layer 1. Thus, the gas sensor element 100A differs from the gas sensor element 100 in that a larger area is surrounded by the first porous protective layer 31A.

When the first porous protective layer 31A, which does not contain La or the like, surrounds not only the porous diffusive resistance layer 2 but also the shielding layer 1, that is, when the area of the detection portion 10 that is directly surrounded by the first porous protective layer 31A, which does not contain La or the like, is increased, it becomes possible to further increase the effect of reducing the output change.

In addition, as the gas sensor element 100A also has a second porous protective layer 32A, which is made of an alumina material, contains La and the like, and is formed such that it surrounds the first porous protective layer 31A, the strength of the porous protective layer 30A as a whole is ensured.

(Experiments for Verifying the Performance of the Gas Sensor Element of the Present Invention and Results Thereof)

The inventors conducted experiments for verifying the performance of the gas sensor element of the present invention. More specifically, the inventors verified the output change of the sensor before and after the sensor is poisoned, and also verified the degree of influence of S poisoning in each area of the porous protective layer, and further verified the output change rate as well as the CS (cold chute) convergence time, which indicates a time from the time the output value is shifted to the rich side immediately after the engine is started till the time the output value converges to the normal value, for when the concentration of La in the second porous protective layer is changed, so as to verify the bond strength of the porous protective layer.

Figure 3:
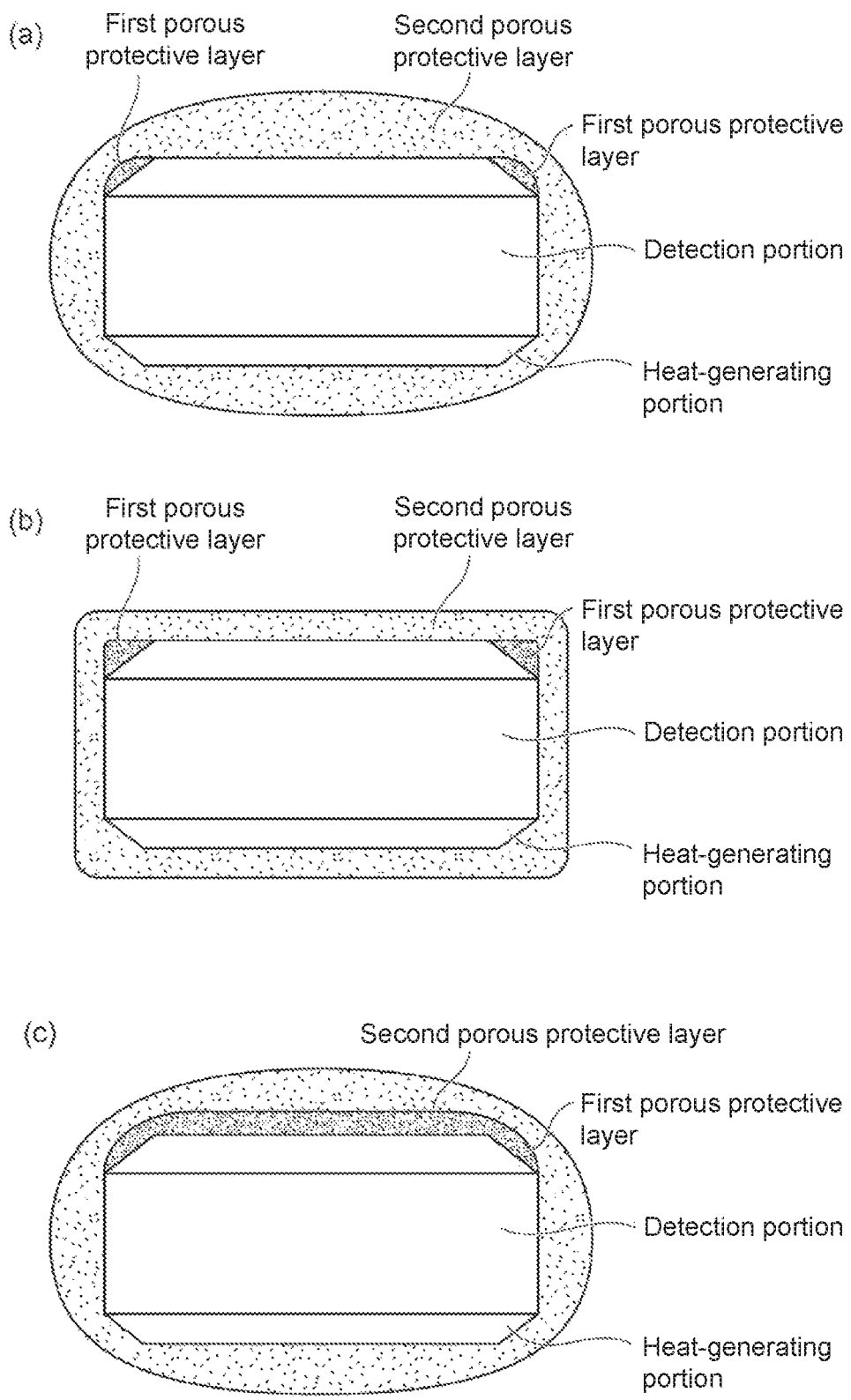
FIG. 3 are schematic views showing gas sensor elements used for experiments; specifically, FIGS. 3(*a*), 3(*b*), and 3(*c*) are views showing gas sensor elements of Examples 1, 2, and 3, respectively.

First, FIGS. 3(a), 3(b), and 3(c) are views showing Examples 1, 2, and 3 of the gas sensor elements used for the experiments, respectively. A sample of Example 1 shown in FIG. 3(a) is the one obtained by simulating the gas sensor element 100 shown in FIG. 1. A sample of Example 2 shown in FIG. 3(b) is the one obtained by forming the second porous protective layer in a rectangular parallelepiped shape. The sample of Example 3 shown in FIG. 3(c) is the one obtained by simulating the gas sensor element 100A shown in FIG. 2.

Figure 4:
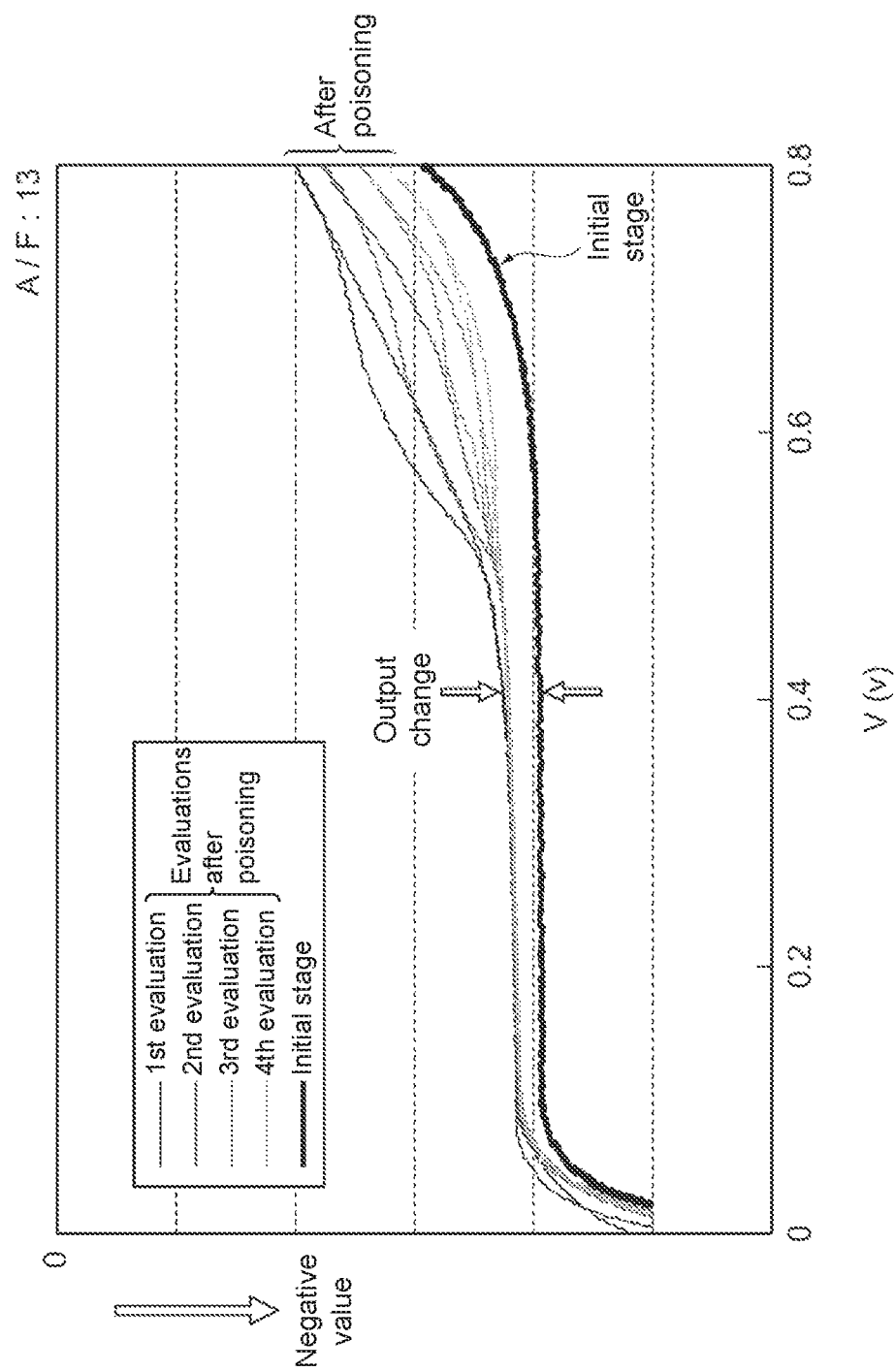
FIG. 4 is a view showing an output change of a sensor before and after the sensor is poisoned.

First, FIG. 4 shows the verification results of an output change of a sensor before and after the sensor is poisoned. A gas sensor element with the conventional structure was used, and the element was exposed to a high-concentration $SO_2$ gas atmosphere, which is unlikely in the real environment, to closely examine the sensor characteristics, such as gas response, using a model gas apparatus.

FIG. 4 can verify that the sensor output becomes low on the rich side. Further, it was also found that S was adsorbed strongly locally as $SO_4^{2-}$ onto La in the porous protective layer through high-sensitivity analysis of the surface and the fracture cross-section of the sensor element at that time.

FIG. 4 can also confirm that the output change of the sensor does not recover even when the ordinary characteristic evaluation is repeated.

Then, as a result of investigating the conditions for the recovering the output, it was found that quite rich conditions and an increase in the element temperature are necessary to recover the output.

It is considered that $SO_4^{2-}$ that had been adsorbed onto La will be reductively desorbed under such conditions. However, as such conditions are difficult to create in the actual engine operation, it was found necessary to provide a structure in which such an output change does not occur.

Figure 5:
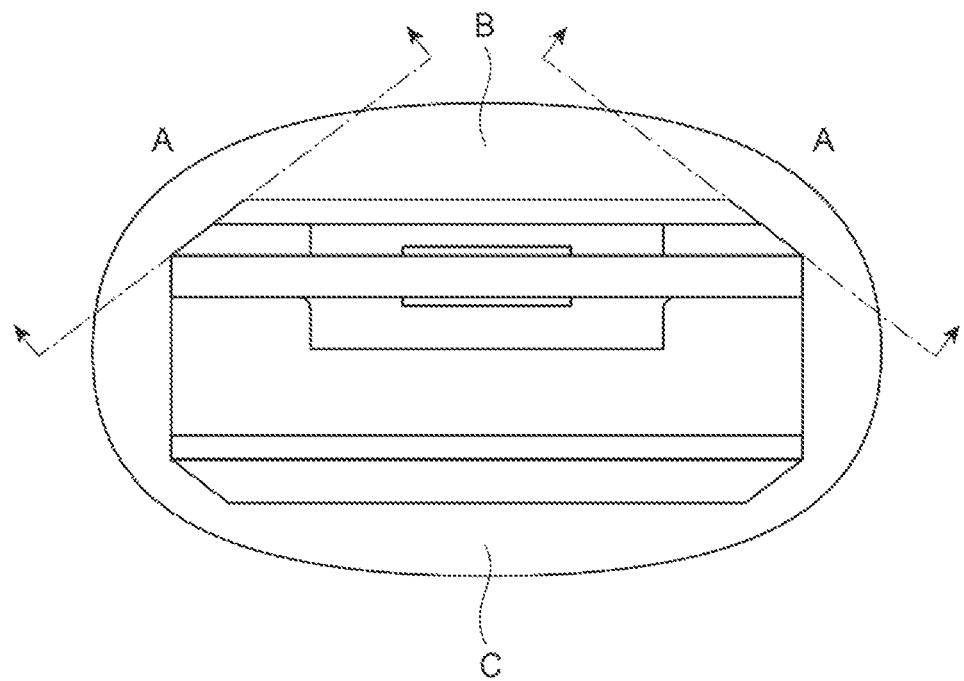
FIG. 5 is a schematic view illustrating the degree of influence on the output change of the sensor for each area of the porous protective layer.

Next, the degree of influence of S poisoning in each area of the porous protective layer was investigated. Consequently, as shown in FIG. 5, it was found that the degree of influence in neighboring areas A of the porous diffusive resistance layer is 77%, that in an area B, which is adjacent to the shielding layer, is about 15%, and that in a wide range of other areas C is about 8%.

From the above verification results, it was clarified that the output change of the sensor can be effectively suppressed if S poisoning in the neighboring areas A of the porous diffusive resistance layer is suppressed.

Figure 6:
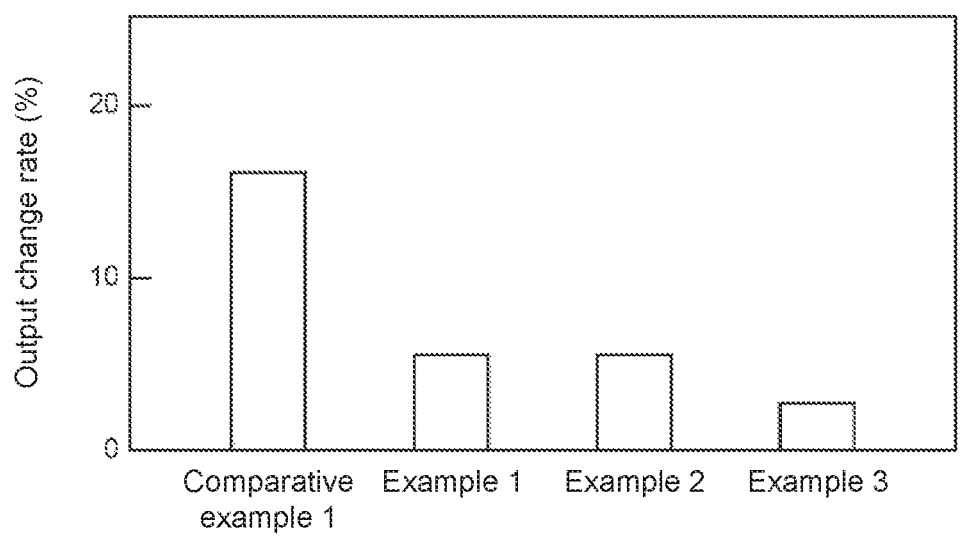
FIG. 6 is a view showing the experimental results related to the output change rate of each of Comparative Example 1 and Examples 1 to 3.

First, the output change rates of the sensors were verified using Examples 1 to 3 and Comparative Example 1 (the configuration of the conventional product in which the first porous protective layer also contains La). FIG. 6 shows the verification results.

FIG. 6 can confirm that the output change rate of Comparative Example 1 is 17%, those of Examples 1 and 2 were reduced to 6%, and that of Example 3 was reduced to 3%. With regard to Example 3, it is considered that as the area of the first porous protective layer, which does not contain La, was increased, the influence of S poisoning in the detection portion was further reduced, which led to a further reduction of the output change rate.

Figure 7:
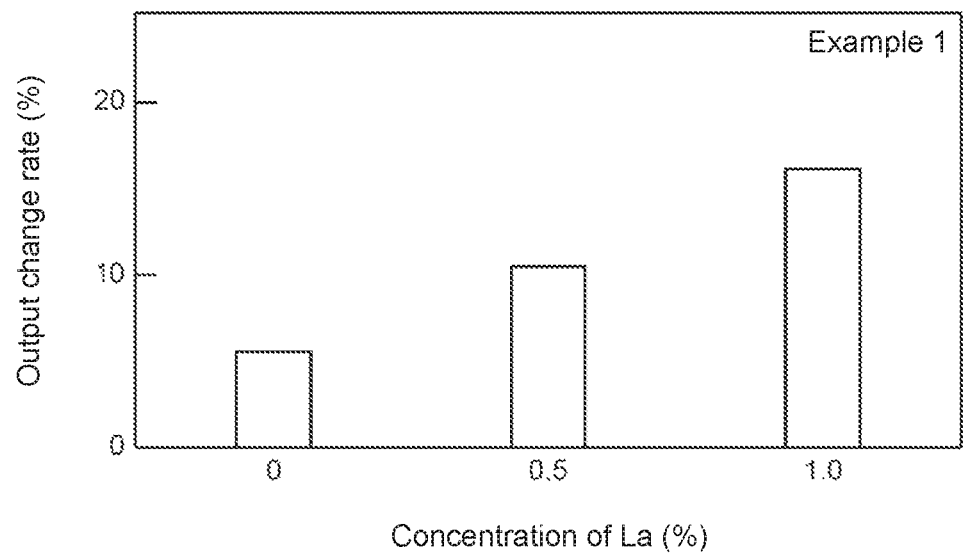
FIG. 7 is a view showing the experimental results related to the output change rate when the concentration of La in the second porous protective layer is changed in Example 1.
Figure 8:
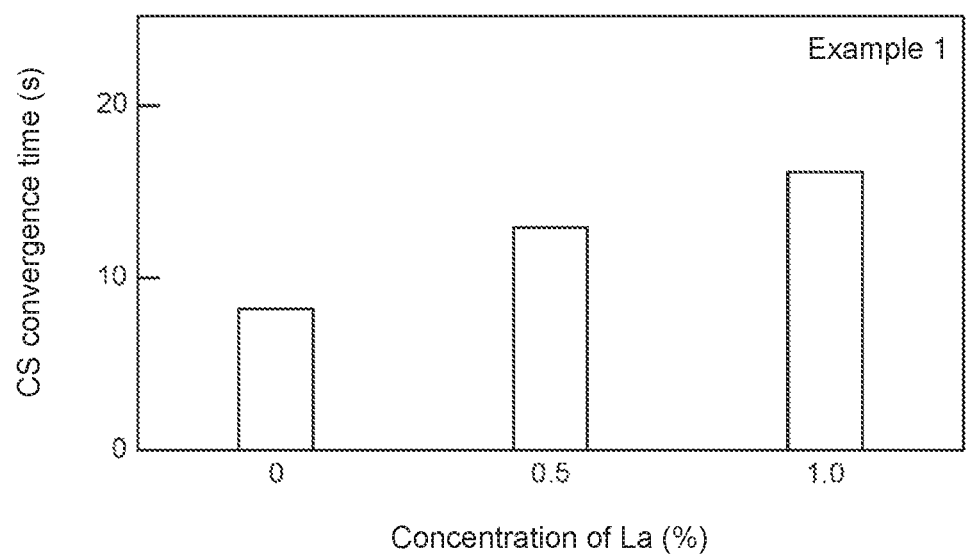
FIG. 8 is a view showing the experimental results related to the CS (cold chute) convergence time when the concentration of La in the second porous protective layer is changed in Example 1.

Next, FIG. 7 shows the experimental results related to the output change rate when the concentration of La in the second porous protective layer was changed, and FIG. 8 shows the experimental results related to the CS (cold chute) convergence time.

FIG. 7 can confirm that the lower the concentration of La, the lower the output change rate. However, it has been also found that La is preferably contained from a viewpoint of the strength and the stability of alumina that forms the porous protective layer. Thus, taking all of these into consideration, it can be concluded that La is preferably contained in the second porous protective layer in the range of greater than 0 mass % and less than or equal to 1 mass %.

In addition, From FIG. 8, results of the CS convergence time that show a similar tendency to the output change rate were obtained.

Figure 9:
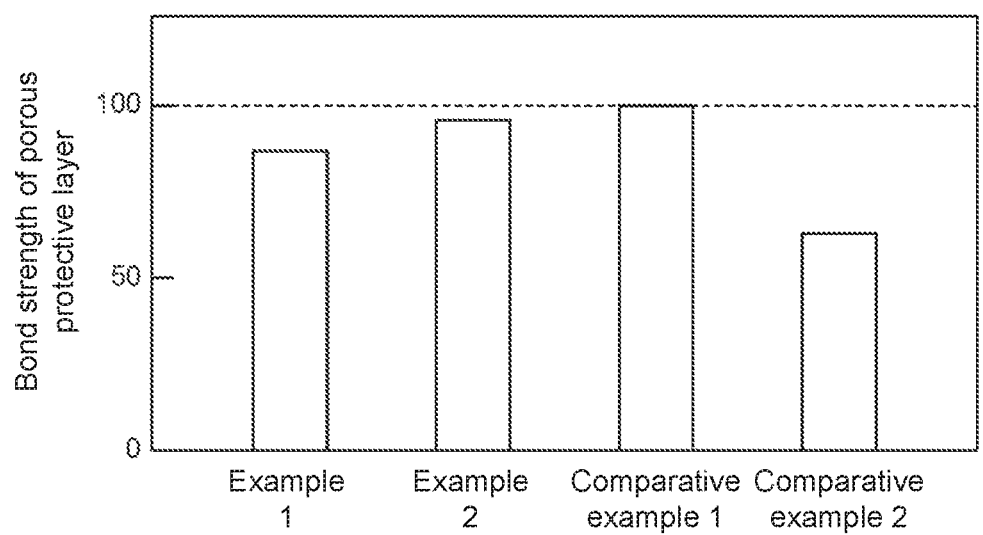
FIG. 9 is a view showing the experimental results related to the bond strength of the porous protective layer of each of Examples 1 and 2 and Comparative Examples 1 and 2.

Further, FIG. 9 is a view showing the experimental results related to the bond strength of the porous protective layer of each of Examples 1 and 2 and Comparative Examples 1 and 2.

It was verified that when the bond strength of Comparative Example 1 in which both the first and second porous protective layers contain La is represented by Reference 100, Example 2 can obtain a bond strength of about 95, which is about equal to the bond strength of Comparative Example 1, and Example 1 can also obtain a bond strength of about 85, and thus that, sufficient bond strength can be obtained even when the first porous protective layer does not contain La.

Although the embodiments of the present invention have been described in detail with reference to the drawings, specific structures are not limited thereto, and any design changes that may occur within the spirit and scope of the present invention are all included in the present invention.

REFERENCE SIGNS LIST

1 Shielding layer
2 Porous diffusive resistance layer
3 Solid electrolyte layer
4 Pair of electrodes
41 Electrode on the measurement target gas side
42 Electrode on the reference gas side
5 Reference gas space protective layer
6 Heat generation source (heater)
7 Heat generation source substrate
8a Measurement target gas space
8b Reference gas space
10 Detection portion
20 Heating portion
30,30A Porous protective layer
31,31A First porous protective layer
32,32A Second porous protective layer
100,100A Gas sensor element

The invention claimed is:

1. A gas sensor element comprising:
a detection portion including
a solid electrolyte layer having a pair of electrodes on opposite sides thereof, the pair of electrodes including an electrode on a measurement target gas side and an electrode on a reference gas side,
a porous diffusive resistance layer that surrounds the electrode on the measurement target gas side with a measurement target gas space interposed therebetween,
a shielding layer that defines the measurement target gas space with the porous diffusive resistance layer, and
a reference gas space protective layer that surrounds the electrode on the reference gas side with the reference gas space interposed therebetween;
a heat-generating portion stacked on the detection portion, the heat-generating portion having a heat generation source; and
a porous protective layer that surrounds the detection portion and the heat-generating portion, wherein
the porous protective layer includes a first porous protective layer and a second porous protective layer, the first porous protective layer surrounding at least the porous diffusive resistance layer, and the second porous protective layer surrounding the first porous protective layer and also surrounding the detection portion and the heat-generating portion,
the first porous protective layer contains none of La, Ca, or Mg, and
the second porous protective layer contains La, wherein a content of La in the second porous protective layer is in a range of greater than 0 mass % and less than or equal to 1 mass %.

2. The gas sensor element according to claim 1, wherein the first porous protective layer surrounds the porous diffusive resistance layer and the shielding layer.

* * * * *